United States Patent [19]
Baxter et al.

[11] Patent Number: 5,512,566
[45] Date of Patent: Apr. 30, 1996

[54] TRICYCLIC COMPOUNDS HAVING AFFINITY FOR THE 5-HT1A RECEPTOR

[75] Inventors: Ellen W. Baxter, Glenside; Allen B. Reitz, Lansdale, both of Pa.

[73] Assignee: Ortho Pharmaceutical Corporation, Raritan, N.J.

[21] Appl. No.: 142,748

[22] Filed: Oct. 25, 1993

[51] Int. Cl.$^6$ ............ C07D 471/04; C07D 498/04; A61K 31/435; A61K 31/535
[52] U.S. Cl. ............ 514/230.2; 514/292; 544/101; 546/86; 546/87
[58] Field of Search ............ 544/101; 546/86, 546/87; 514/230.2, 292

[56] References Cited

U.S. PATENT DOCUMENTS 3,755,584  8/1973  Plotnikoff ............ 424/263

OTHER PUBLICATIONS

Cecil Textbook of Medicine, 19th ed. (1992), Wyngaarden, M.D. editor, pp. 2075–2078.
Synthesis of 2,3,4,4a,5,6—Hexahydro—1(H)—Pyrazino[1,2—a]Quinoline & Its 3—Substituted Derivatives; (Miss) V. Aruna Rao, et al.; Communication No. 1389, pp. 833–835, Ind. J. Chem (1969).
Berend Olivier, et al.; Serenics; DN&P 3(5), Jun. 1990, pp. 261–271.
D. S. Charney, M.D., et al.; Serotonin—Specific Drugs For Anxiety And Depressive Disorders, pp. 437–446, Annu. Rev. Med. 41 (1990).
Naresh Kumar, et al., Agents Acting On CNS: Part XXVIII–Synthesis Of 3—Substituted 2,3,4,4a,5,6—Hexahydro—1(H)—Pyrazino[1,2—a]Quinoxaline Disorders, pp. 244–245, Indian Journal of Chemistry, vol. 17B, Mar. 1979.

S. P. Gupta, et al., Compounds Acting On CNC: Part XXII—Synthesis of 2,3,4,4a,5,6—Hexahydro—1(H)—Pyrazineo[2,1—c]—1,4—Benzoxazines, Indian Journal of Chemistry, vol. 13, May 1975, pp. 462–467.
James S. New, Ph.D., The Discovery And Development Of Buspirone: A New Approach To The Treatment Of Anxiety, Medicinal Research Reviews, vol. 10, No. 3, 283–326 (1990).
Joel R. Huff, et al., Bioactive Conformation Of 1—Arylipiperazines At Central Serotonin Receptors, J. Med. Chem. 1985, 28, 945–948.
V. Aruna Rao, et al. Agents Acting On The Central Nervous System. XIII. 2,3,4,4A,5,6—Hexahydro—1(H)—Pyrazino[1,2—A]Quinolines. A New Class Of Hypotensive Agents, Journal of Medicinal Chemistry, 1970, vol. 13, No. 3, pp. 516–522.
Micheal D. Ennis, et al., Novel Indolodioxanes With Antihypertensive Effects: Potent Ligands For The 5—HT$_1$A Receptor, J. Med. Chem. 35 (1992), pp. 3058–3066.
Michael G. N. Russell, et al., Benz[f]Isoquinoline Analogues As High–Affinity σ Ligands, Journal of Medicinal Chemistry, 1992, vol. 35, No. 11, pp. 2025–2033.

*Primary Examiner*—Philip I. Datlow
*Attorney, Agent, or Firm*—Ralph R. Palo

[57] ABSTRACT

Compounds represented by the general formula I:

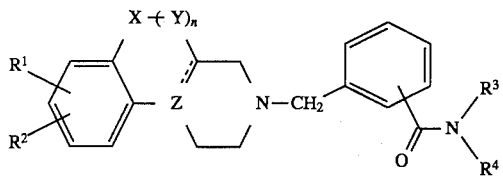

are disclosed as useful in treating diseases of the central nervous system.

10 Claims, No Drawings

TRICYCLIC COMPOUNDS HAVING AFFINITY FOR THE 5-HT1A RECEPTOR

BACKGROUND OF THE INVENTION

Compounds which modulate serotonergic receptors are known to have a therapeutic use in man for the treatment of anxiety, schizophrenia, depression, convulsions, migraine, insomnia, and other diseases of the central nervous system. Further, such ligands may be useful in treating cardiovascular disorders such as hypertension (e.g. *J. Med. Chem*, 1992, 35, 3058–3066). Partial agonists of the serotonin-1A (5-HT$_{1A}$) receptor have been found to be useful for the treatment of anxiety; a compound of this type is buspirone, marketed as an anxiolytic (*Med. Res. Rev*, 1990, 10, 283–326; *Annu. Rev. Med*, 1990, 41,437–446). In addition, compounds modulating the 5-HT$_{1A}$ site may be useful as antiagressives or serenics (*Drug News Perspect*, 1990, 3, 261–271).

Compounds having some structural similarity to those of the present invention are described in European Patents 463691 and 485952, World Patents 9119719, 9304682, and 9304684 as well as Rao, V. A.; Jain, P. C.; Anand, N. *Ind. J. Chem.* 1969, 7, 833, Rao, V. A.; Jain, P. C.; Anand, N.; Srimal, R. C.; Dua, P. R. *J. Med. Chem.* 1970, 13, 516, Gupta, S. P.; Chatterjee, S. S.; Bindra, J. S.; Jain, P. C.; Anand, N. *Ind. J. Chem.* 1975, 13, 462, Kumar, N.; Jain, P. C.; Anand, N. *Ind. J. Chem.* 1979, 17B, 244, Huff, J. R.; King, S. W.; Saari, W. S.; Springer, J. P.; Martin, G. E.; Williams, M., *J. Med. Chem.* 1985, 28, 945; Russell, M. G. N.; Baker, R.; Billington, D. C.; Knight, A. K.; Middlemiss, D. N.; Noble, A. J. *J. Med. Chem.* 1992, 35, 2025.

SUMMARY OF THE INVENTION

The present invention is directed to compounds represented by the general formula I:

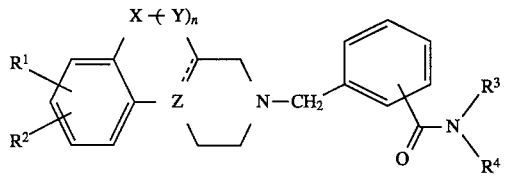

wherein $R^1$, $R^2$, $R^3$, $R^4$, X, Y, Z and n are as defined hereinafter. Such compounds are a novel structural class which have potent affinity for the 5-HT$_{1A}$ receptor and may thus be expected to be useful in treating anxiety, aggression, schizophrenia, depression, convulsion migraines, insomnia and other diseases of the central nervous system.

DETAILED DESCRIPTION OF THE INVENTION

More particularly, the present invention is directed to compounds represented by the general formula I:

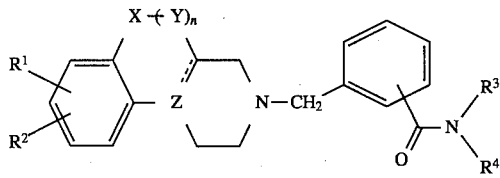

$R^1$ and $R^2$ are independently selected from any of H, halogen, $C_1$–$C_6$ alkoxy, $C_1$–$C_6$ alkyl or trifluoromethyl. More preferably, each of $R^1$ and $R^2$ is H.

X is O when n is 1 and X is NH when n is 0.

Y is CH$_2$.

n is 0 or 1.

Z is N when X is O or Z is C when X is NH.

$R^3$ and $R^4$ are independently selected from any of H, $C_1$–$C_6$ alkyl, $C_1$–$C_8$ acyl, provided that $R^3$ and $R^4$ can not be $C_1$–$C_8$ acyl at the same time, or may be taken together to form together with the N a monocyclic 5–7 membered saturated ring or a 5–7 membered ring fused to an aromatic ring aryl. More preferably, $R^3$ and $R^4$ are taken together to form together with the N a 6 membered saturated ring with carbon atoms at the other 5 ring positions or a bicyclic ring structure of the formula:

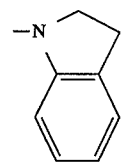

The substitution pattern in the amide-bearing aromatic ring is ortho, meta, or para.

As used herein alkyl and alkoxy include straight and branched chains. For example, alkyl radicals include methyl, ethyl, propyl, isopropyl, n-butyl, isobutyl, sec-butyl, t-butyl, n-pentyl, 2-methyl-3-butyl, 1-methylbutyl, 2-methylbutyl, neopentyl, n-hexyl, 1-methylpentyl, 3-methylpentyl. Alkoxy radicals are oxygen ethers formed from the previously described straight or branched chain alkyl groups. The term "independently" is used with respect to aryl and ring substituents to indicate that when more than one of such substituents is possible such substituents may be the same or different from each other. The term "aryl," as used herein alone or in combination with other terms, indicates aromatic hydrocarbon groups such as a phenyl or naphthyl group.

Examples of particularly preferred compounds are:

1-(3-(2-(1,2,3,4-Tetrahydro-9H-pyrido(3,4-b)indolyl)methyl)benzoyl)piperidine;

1-(3-(2-(1,2,3,4-Tetrahydro-9H-pyrido(3,4-b)indolyl)methyl)benzoyl)indoline;

1-(3-(1-(1,2,3,4,4a,5-Hexahydropyrazino(1,2-c)-1,4-benzoxazinyl)methyl)benzoyl)piperidine and 1-(3-(3-(1,2,3,4,4a,5-Hexahydropyrazino(1,2-c)-1,4-benzoxazinyl)methyl)benzoyl)indoline.

The definition of formula I includes race mates and individual isomers; e.g., as caused by the presence of an asymmetric carbon such as when a substituent would be 2-butyl. Also within the scope of the invention are compounds of the invention in the form of hydrates and other solvate forms.

Representative salts of the compounds of formula I which may be used include those made with acids such as hydrochloric, hydrobromic, hydroiodic, perchloric, sulfuric, nitric, phosphoric, acetic, propionic, glycolic, lactic, pyruvic, oxalic, malonic, succinic, maleic, fumaric, malic, tartaric, citric, benzoic, cinnamic, mandelic, methanesulfonic, ethanesulfonic, hydroxyethanesulfonic, benzenesulfonic, p-toluenesulfonic, cyclohexanesulfamic, salicyclic, p-amino-salicyclic, 2-phenoxybenzoic, 2-acetoxybenzoic or a salt made with saccharin. Such salts can be made by reacting the free base of formula I with the acid and recovering the salt.

The compounds of Formula I may be prepared according to the Reaction Scheme 1:

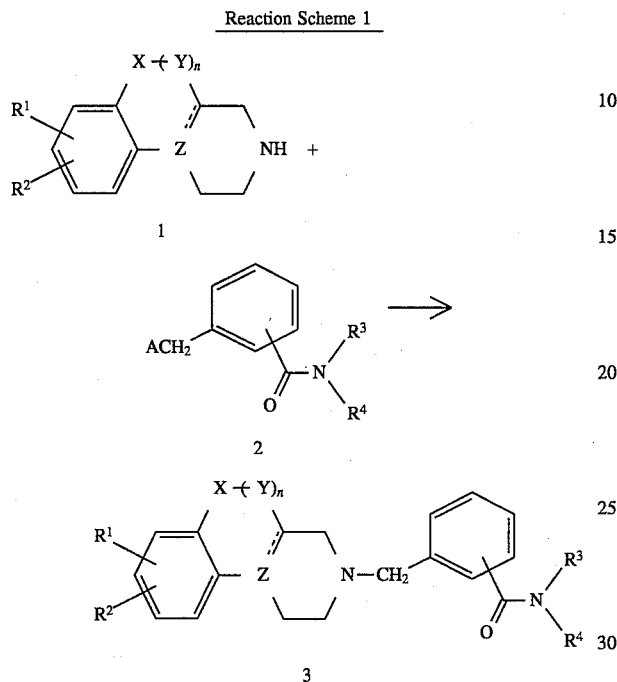

Tricyclic amines 1 can be reacted with a halomethylbenzamide 2 (wherein A is a halogen) to afford compound 3. These condensations can be carried out in THF or a polar aprotic solvent such as DMSO or DMF in the presence of a base such as triethylamine or potassium carbonate and generally requiring heating from about 30°–80° C.

Tricyclic compounds 1 are either commercially available or may be prepared as shown in Reaction Scheme 2. Phthalimide 4 (Gupta, S. P. et al. *Ind. J. Chem.* 1975, 13, 462) can be converted to benzoxazine 5 using standard catalytic hydrogenation conditions with Raney nickel or palladium on carbon. Cleavage of the phthalimido group can be effected with hydrazine in a refluxing alcoholic solvent such as ethanol to provide diamine 6. Condensation with benzylchloroformate can be carried out in an aprotic solvent such as tetrahydrofuran or dichloromethane with a base such as triethylamine or pyridine present. These additions are usually done at a low temperature (–78° C. to 0° C.), and then the reaction mixture is allowed to warm to ambient temperature. The subsequent reaction with chloroacetyl chloride can be conducted under the same reaction conditions to provide 7. Ring closure of 7 can be effected with mild base such as potassium carbonate in a polar aprotic solvent such as N,N-dimethylformamide or dimethyl sulfoxide at room temperature. Reduction of the lactam can be achieved with a borane reagent such as a borane-tetrahydrofuran complex in tetrahydrofuran as solvent. Removal of the carbobenzyloxy group can be done under transfer hydrogenation conditions such as 1,4-cyclohexadiene with palladium on carbon with acid in an aqueous alcoholic solvent system to give 8.

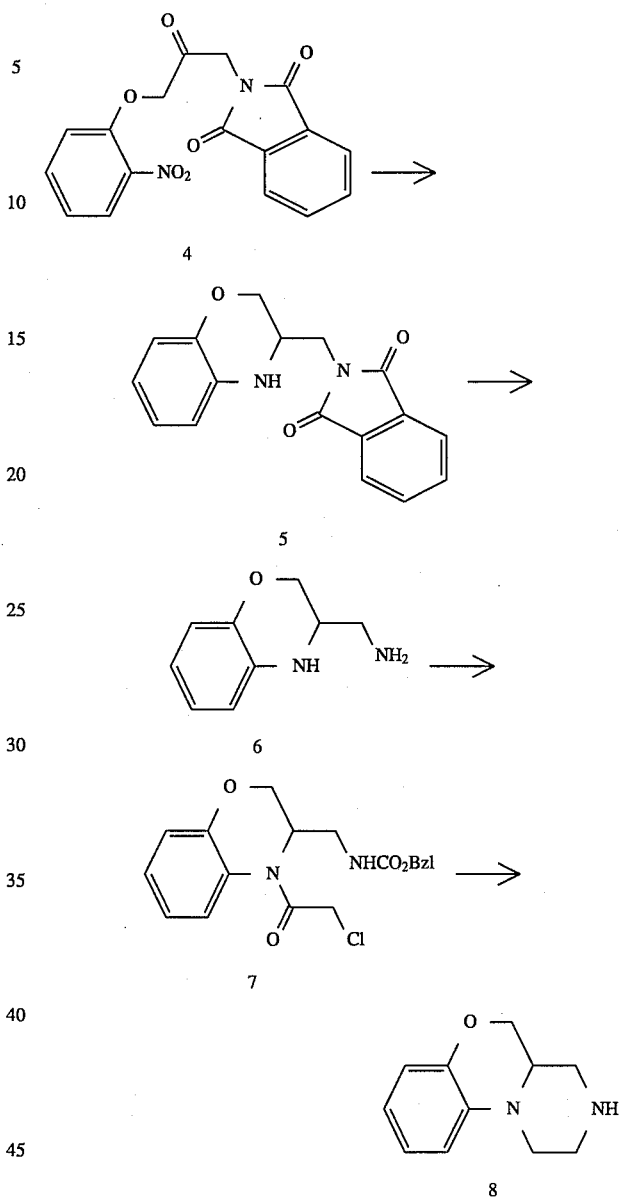

Preparation of halomethylbenzamides 2 can be achieved as shown in Reaction Scheme 3. An amine and halomethylbenzoyl chloride (wherein A is a halogen) are combined at about 0° C. in an aprotic solvent such as tetrahydrofuran or dichloromethane and the mixture is then allowed to warm to about 25° C. to ensure complete reaction.

Reaction Scheme 3

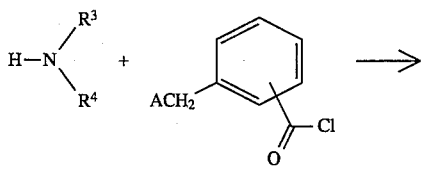

-continued
Reaction Scheme 3

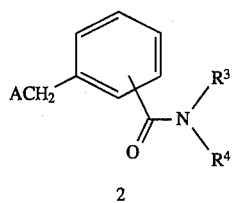

2

The final products are preferably chromatographed to achieve purity and are then converted to an acceptable salt form.

To prepare the pharmaceutical compositions of this invention, one or more compounds or salts thereof of the invention, as the active ingredient, is intimately admixed with a pharmaceutical carrier according to conventional pharmaceutical compounding techniques, which carrier may take a wide variety of forms depending on the form of preparation desired for administration, e.g., oral or parenteral. In preparing the compositions in oral dosage form, any of the usual pharmaceutical media may be employed. Thus for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage form, in which case solid pharmaceutical carriers are obviously employed. If desired, tablets may be sugar coated or enteric coated by standard techniques. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed. The pharmaceutical compositions herein will contain per dosage unit; e.g., tablet, capsule, powder, injection, teaspoonful and the like, from about 50 to about 100 mg of the active ingredient.

In therapeutic use as an agent useful in treating diseases of the central nervous system in mammals, particularly humans, the compounds utilized in the pharmaceutical method of this invention are administered to the patient at dosage levels of from about 0.1 to 10 mg/kg per day. The dosages, however, may be varied depending upon the requirements of the patient, the severity of the condition being treated, the particular disease being treated and the compound being employed. Determination of optimum dosages for a particular situation is within the skill of the art.

The testing results of representative compounds of this invention are listed in Table 1, in binding at the dopamine-2 ($D_2$) and 5-$HT_{1A}$ receptors. As can be seen in data shown in Table 1, there is weak or no activity at the $D_2$ site, whereas there is pronounced binding to the 5-$HT_{1A}$ site.

TABLE 1

| Compound | Receptor Binding, ($K_i$, nM) | |
| --- | --- | --- |
|  | D-2 | 5-$HT_{1A}$ |
| 9 | 374 | 13 |
| 11 | >1000 | 9.2 |
| 13 | >1000 | 12 |

TABLE 1-continued

| Compound | Receptor Binding, ($K_i$, nM) | |
|---|---|---|
| | D-2 | 5-HT$_{1A}$ |
| 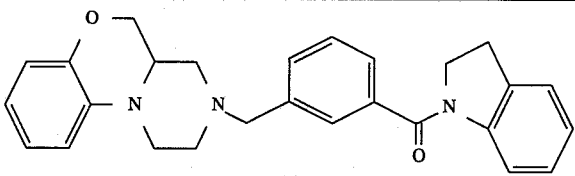 14 | >1000 | 6.5 |

Receptor Binding Assay

The dopamine $D_2$ and serotonin 5-HT$_{1A}$ binding activity of compounds was determined using a $P_2$ fraction (synaptosomal membranes) prepared from male, Wistar rats. The $D_2$ assay employed a $P_2$ fraction from the striatum, the ligand $^3$H-spiperone at a concentration of 0.05 nM, and 1 nM haloperidol as a blank determinant. Incubation was in 3 mM potassium phosphate buffer having a pH of 7.5 for 45 min at 37° C. Under these conditions, specific binding constituted 75% of total binding, and the $K_I$ values for some known drugs were: 0.37 nM for haloperidol and 82 nM for clozapine.

The 5-HT$_{1A}$ assay used a $P_2$ fraction from the cerebral cortex, the ligand $^3$H-8-hydroxy-DPAT at a concentration of 3 nM, and 1 mM serotonin as a blank determinant. Incubation was in 3 mM potassium phosphate buffer having a pH of 7.5 for 20 min at 25° C. Under these conditions, specific binding constituted 85% of total binding, and the $K_I$ values for some known drugs were: 0.32 nM for WB4101, 59 nM for phentolamine, and 111 nM for clozapine.

The data from each assay were analyzed by calculating the percent inhibition of the binding of the tritiated ligands by given concentrations of the test compound. $K_I$ values, where given, were obtained from the logit analysis of concentration-inhibition curves.

EXAMPLES

Example 1

1-(3-(2-(1,2,3,4-Tetrahydro-9H-pyrido(3,4-b)indolyl)methyl)-benzoyl)piperidine Monooxalate 0.3 Hydrate (9)

To an ice-cooled solution of piperidine (67.6 g, 0.793 mole) in tetrahydrofuran (1 L) was added dropwise a solution of 3-chloromethylbenzoyl chloride (100.0 g, 0.529 mmol). When the addition was complete, the reaction mixture was allowed to warm to ambient temperature and was left to stir overnight. The reaction mixture was poured into a solution of 1N hydrochloric acid. This solution was extracted with diethyl ether. The ether extracts were combined, washed with water, dried (MgSO$_4$), and concentrated to afford 108.7 g (86%) of N-(3-(chloromethyl)benzoyl)piperidine (10) as a pale yellow oil whose $^1$H NMR in CDCl$_3$ supported the structure.

To a solution of 1,2,3,4-tetrahydro-9H-pyrido(3,4-b)indole (2.50 g, 14.5 mmol) in 50 mL of tetrahydrofuran was added benzyl chloride 10 (4.14 g, 17.4 mmol) in 50 mL of tetrahydrofuran followed by triethylamine (1.91 g, 18.9 mmol). This suspension was refluxed under nitrogen for 30 h. After cooling, the reaction mixture was poured into 1N hydrochloric acid and diethyl ether. The layers were separated, and the aqueous solution was basified with solid potassium carbonate and then extracted with chloroform. The chloroform extracts were combined, dried (Na$_2$SO$_4$), and concentrated to afford an orange-brown oil which was purified by column chromatography on flash silica gel (chloroform to 5% methanol-chloroform) to provide a yellow foam. This material was dissolved in methanol, and oxalic acid (0.81 g) was added followed by diethyl ether and hexanes. A buff-colored solid was collected which was recrystallized from methanol and ether to provide 1.41 g (21%) of 9 as a beige powder, mp 173°–181° C. The $^1$H NMR in DMSO-d$_6$ supported the assigned structure. $^1$H NMR δ1.50 (br m, 4H), 1.61 (br s, 2H), 2.84 (br s, 2H), 3.15 (br s, 2H), 3.28 (br s, 2H), 3.59 (br s, 2H), 3.92 (s, 2H), 4.12 (s, 2H), 6.95–7.07 (m, 2H), 7.28–7.55 (m, 6H).

Elemental analysis: Calculated for C$_{24}$H$_{27}$N$_3$O•1.0C$_2$H$_2$O$_4$•0.3H$_2$O: C, 66.59; H, 6.36; N, 8.96; H$_2$O, 1.15. Found C, 66.19; H, 6.32; N, 9.08; H$_2$O, 0.81.

Example 2

1-(3-(2-(1,2,3,4-Tetrahydro-9H-pyrido(3,4-b)indolyl)methyl)benzoyl)indoline Monofumarate (11)

To an ice-cooled solution of indoline (1.50 g, 12.6 mmol) and triethylamine (1.66 g, 16.3 mmol) in tetrahydrofuran (50 mL) was added dropwise 3-chloromethylbenzoyl chloride (2.86 g, 15.1 mmol). When the addition was complete, the reaction mixture was allowed to warm to ambient temperature and was left to stir overnight. The reaction mixture was poured into saturated sodium bicarbonate solution. This solution was extracted with chloroform. The chloroform extracts were combined, washed with water, dried (Na$_2$SO$_4$), and concentrated to afford 3.23 g (79%) of a pale yellow oil of N-(3-(chloromethyl)benzoyl)indoline (12) whose $^1$H NMR in CDCl$_3$ supported the structure.

To a solution of 1,2,3,4-tetrahydro-9H-pyrido(3,4-b)indole (3.11 g, 18.1 mmol) in tetrahydrofuran (100 mL) was added benzyl chloride 12 (6.50 g, 23.9 mmol) in tetrahydrofuran (100 mL) followed by triethylamine (4.57 g, 45.2 mmol). This suspension was refluxed under nitrogen for 2.5 days. After cooling, the reaction mixture was poured into 1N hydrochloric acid and diethyl ether. The layers were separated; the ether extract was washed with saturated sodium bicarbonate solution, dried (MgSO$_4$), and concentrated to provide a beige foam. The aqueous solution was basified with solid potassium carbonate and then extracted with chloroform. The chloroform extracts were combined, dried (Na$_2$SO$_4$), and concentrated to afford a beige foam. Since both materials appeared to contain the desired product, they were combined and purified by column chromatography on flash silica gel (chloroform) to provide a brown foam. This material was dissolved in methanol, and fumaric acid (0.76 g) was added followed by diethyl ether and hexanes. A cream-colored precipitate was collected which was recrystallized from acetone to provide 2.03 g (21%) of 11 as a buff-colored powder, mp 215°–217° C. The $^1$H NMR in DMSO-$d_6$ supported the assigned structure. $^1$H NMR, δ2.70 (br m, 2H), 2.84 (br t, 2H), 3.09 (t, J=8.2 Hz, 2H), 3.61 (br s, 2H), 3.82 (br s, 2H), 4.02 (t, J=8.2 Hz, 2H), 6.62 (s, 2H), 6.90–7.02 (m, 3H), 7.12 (br s, 1H), 7.26 (m, 3H), 7.35 (d, J=7.5 Hz, 1H), 7.50–7.57 (m, 3H).

Elemental analysis: Calculated for $C_{27}H_{25}N_3O$•1.0 $C_2H_2O_4$: C, 71.11, H, 5.58; N, 8.03. Found C, 70.96; H, 5.56; N, 8.44.

Example 3

1-(3-(1-(1,2,3,4,4a,5-hexahydropyrazino(1.2-c)-1,4-benzoxazinyl)methyl)benzoyl)pipridine Sesquioxalate (13)

The preparation of 3-aminomethyl-1,4-benzoxazine (6) was carried out by the method of Gupta et al. (*Ind. J. Chem.* 1975, 13, 462) with the following modification. Reduction of the nitro group with concomitant reductive amination was conducted with 10% palladium on charcoal rather than Raney nickel.

A solution of diamine 6 (1.80 g, 11.0 mmol) and triethylamine (1.66 g, 16.4 mmol) in tetrahydrofuran (100 mL) was cooled to –78° C. under nitrogen. To this solution was added dropwise benzylchloroformate (2.24 g, 13.2 mmol) in tetrahydrofuran (100 mL). When the addition was complete, the reaction mixture was allowed to warm slowly to ambient temperature. After 3 days of stirring, the reaction mixture was poured into saturated sodium bicarbonate solution which was extracted with chloroform. The chloroform extracts were combined, dried ($Na_2SO_4$), and concentrated to provide the desired carbamate as 3.80 g (quantitative yield) of a dark brown oil whose $^1$H NMR in $CDCl_3$ supported the expected structure. This material was taken on without further purification.

A solution of the carbamate (3.80 g, 12.8 mmol) and triethylamine (2.19 g, 21.7 mmol) in dichloromethane (250 mL) was cooled to –78° C. under nitrogen. To this solution was added dropwise chloroacetyl chloride (1.73 g, 15.3 mmol) as a solution in dichloromethane (100 mL). When the addition was complete, the reaction mixture was slowly warmed to ambient temperature. After stirring overnight, the reaction mixture was poured into water. The layers were separated, and the organic layer was washed with 1N hydrochloric acid, dried ($Na_2SO_4$), and concentrated to give 4.77 g (97%) of chloroacetamide 7 as a brown foam. The $^1$H NMR in $CDCl_3$ supported the structure. This material was carried on to the next reaction without further purification.

A suspension of chloroacetamide 7 (4.65 g, 12.4 mmol) and potassium carbonate (5.40 g, 39.1 mmol) in dimethyl sulfoxide (300 mL) was stirred under nitrogen at ambient temperature. After 16 h, the reaction mixture was poured into water and extracted several times with ethyl acetate. The ethyl acetate extracts were combined, washed with water several times, dried ($MgSO_4$), and concentrated to provide a brown foam. Purification was done using column chromatography on flash silica gel (MeOH/chloroform, 0:100 to 1:99) to provide 1.45 g of the expected lactam as a yellow foam. A second purification on flash silica gel (chloroform) afforded an additional 0.44 g of the desired lactam. The $^1$H NMR in $CDCl_3$ supported the structure.

A solution of the above lactam (1.44 g, 4.26 mmol) in tetrahydrofuran (100 mL) was cooled to 0° C. under nitrogen, and a 1M solution of boranetetrahydrofuran complex (21.3 mL, 21.3 mmol) was added dropwise. When the addition was complete, the reaction mixture was allowed to warm to ambient temperature. After 16 h of stirring, the reaction mixture was cooled in ice and diluted with water. A few drops of 1N HCl were added, and then the reaction mixture was basified with solid potassium carbonate. The resulting suspension was extracted with chloroform. The chloroform extracts were combined, dried ($Na_2SO_4$), and concentrated to provide 1.45 g (quantitative yield) of the desired tricyclic amine carbamate as a colorless oil which solidified on standing. The $^1$H NMR in $CDCl_3$ supported the structure. This material was carried on to the next reaction without further purification.

To an ice-cooled solution of the aforementioned carbamate (1.31 g, 4.04 mmol) in 230 mL of 9:1 (v/v) methanol-water was added 10% palladium on carbon (1.31 g), 1,4-cyclohexadiene (3.24 g, 40.4 mmol), and trifluoroacetic acid (1.38 g, 12.1 mmol). The reaction mixture was slowly warmed to ambient temperature under nitrogen. After 16 h, the reaction mixture was filtered through dicalite, and the filtrate was concentrated to give a pale-green solid. To this material was added 10% aqueous sodium carbonate solution which was subsequently extracted several times with chloroform. The chloroform extracts were combined, dried ($Na_2SO_4$), and concentrated to provide 0.64 g (83%) of tricyclic amine 8 as a golden brown oil. The $^1$H NMR in $CDCl_3$ supported the assigned structure. This material was carried on to the next reaction without further purification.

To a solution of tricyclic amine 8 (0.96 g, 5.05 mmol) in tetrahydrofuran (50 mL) was added N-(3-(chloromethyl)benzoyl)piperidine (10, 1.44 g, 6.06 mmol) as a solution in tetrahydrofuran (50 mL). Triethylamine (0.77 g, 7.57 mmol) was added, and the reaction mixture was refluxed under nitrogen for 2 days. The reaction mixture was cooled and 1N hydrochloric acid solution and diethyl ether were added. The layers were separated, and the aqueous solution was basified with solid potassium carbonate and then extracted with chloroform. The chloroform extracts were combined, dried ($Na_2SO_4$), and concentrated to afford a red-brown oil. This material was purified by flash column chromatography on silica gel (MeOH/chloroform, 0:100 to 2:98) to afford 0.73 g of 13 as an iridescent yellow foam. This material was dissolved in acetone and oxalic acidodihydrate (0.35 g) was added. After diethyl ether was added, a cloudy solution resulted which was treated with hexanes to give a fluffy cream-colored precipitate. This solid was recrystallized from acetone/ether to provide two crops of product which were combined to afford 0.33 g (12%) of 13 as a cream-colored powder, mp 168°–172° C. (decomposition). The $^1$H NMR in DMSO-$d_6$ supported the assigned structure. $^1$H NMR δ1.50 (br m, 4H), 1.61 (m, 2H), 2.02 (m, 1 H), 2.45 (m, 1H), 2.96 (br d, 1H), 3.04 (br d, 1H), 3.10 (br t, 2H), 3.25 (br s, 2H), 3.55 (br s, 2H), 3.68–3.92 (m, 4H), 4.23 (br d, J=8.4 Hz, 1H), 6.60–6.92 (m, 4H), 7.28–7.48 (m, 4H).

Elemental analysis: Calculated for $C_{24}H_{29}N_3O_2$•1.5 $C_2H_2O_4$: C, 61.59; H, 6.13; N, 7.98. Found C, 61.64; H, 6.21; N, 7.98.

Example 4

1-(3-(3-(1,2,3,4,4a,5-Hexahydropyrazino(1,2-c)-1,4-benzoxazinyl)methyl)benzoyl)iondoline 1.2 Oxalate (14)

To a solution of tricycle 8 (1.15 g, 6.04 mmol) in tetrahydrofuran (100 mL) was added N-(3-(chloromethyl)benzoyl)indoline (12, 1.97 g, 7.25 mmol) as a solution in tetrahydrofuran (100 mL). Triethylamine (1.53 g, 15.1 mmol) was added, and the reaction mixture was refluxed under nitrogen for 20 h. Analysis by thin layer chromatography indicated that a considerable amount of unreacted starting material was present so additional triethylamine (1.53 g) was added. After 24 h of additional reflux, the reaction appeared to be complete. The reaction mixture was cooled and 1N hydrochloric acid solution and diethyl ether were added. The layers were separated, and the ether extract was washed with saturated sodium bicarbonate solution, dried (MgSO$_4$), and concentrated to provide a dark brown oil. The hydrochloric acid solution was basified with solid potassium carbonate and then extracted with chloroform. The chloroform extracts were combined, dried (Na$_2$SO$_4$), and concentrated to afford a brown foam. Thin layer chromatographic analysis indicated that both materials contained desired product so they were combined and purified by flash column chromatography on silica gel (MeOH/chloroform, 0:100 to 1:99) to afford a brown oil. This oil was repurified three times on flash silica gel using pure chloroform as the eluant to provide a golden brown oil which was dissolved in acetone and oxalic acid-dihydrate (0.35 g) was added. When diethyl ether and then hexanes were added, a fluffy cream colored precipitate fell out of solution. This solid was recrystallized from acetone to provide 0.37 g (11%) of 14 as a snow-white powder, mp 197.5°–198.5° C. The $^1$H NMR in DMSO-d$_6$ supported the assigned structure. $^1$H NMR $\delta$2.00 (br t, 1H), 2.35 (m, 1H), 2.69 (br t, 1H), 3.93 (br d, 1H), 3.00 (br d, 1 H), 3.09 (br t, 3H), 3.64–3.92 (m, 3 H), 3.88 (br t, 1H), 4.02 (br t, 2H), 4.21 (br d, J=8.5 Hz, 1H), 6.60–6.72 (m, 3H), 6.75 (br t, 1H), 6.86 (br d, J=7.4 Hz, 1H), 7.03 (br d, 1H), 7.26 (br m, 1H), 7.28 d, J=7.5 Hz, 1H), 7.48–7.62 (br m, 4H).

Elemental analysis: Calculated for $C_{27}H_{27}N_3O_2 \cdot 1.2\ C_2H_2O_4$: C, 65.88; H, 5.98; N, 7.83. Found C, 66.16; H, 5.60; N, 7.61.

We claim:

1. A compound represented by the formula I:

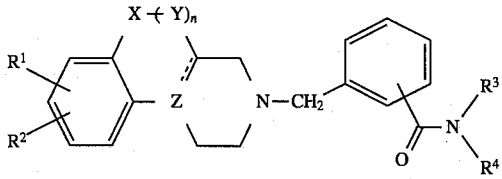

wherein R$^1$ and R$^2$ are independently selected from any of H, halogen, C$_1$–C$_6$ alkoxy, C$_1$–C$_6$ alkyl or trifluoromethyl;

X is O when n is 1 and X is NH when n is 0;

wherein Y is CH$_2$;

wherein n is 0 or 1;

wherein Z is N when X is O and Z is C when X is NH;

wherein R$^3$ and R$^4$ are independently selected from any of H, C$_1$–C$_6$ alkyl, C$_1$–C$_8$ acyl, provided that R$^3$ and R$^4$ can not both be C$_1$–C$_8$ acyl at the same time or may be taken together to form with the N a monocyclic 5–7 membered saturated ring or a 5 membered ring fused to an aromatic ring;

or the racemates, individual isomers, hydrates, solvates or acid addition salts thereof.

2. The compound of claim 1, wherein R$^1$ and R$^2$ are each H.

3. The compound of claim 1, wherein X is O and n is 1.

4. The compound of claim 1, wherein X is NH and n is 0.

5. The compound of claim 1, wherein R$^3$ and R$^4$ are taken together with the N to form a 6 membered saturated ring or together with the N to form a bicyclic ring structure of the formula:

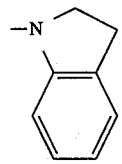

6. The compound of claim 1, wherein R$^3$ and R$^4$ are taken together to form with the N a 6 membered saturated ring.

7. The compound of claim 1, wherein the compound is selected from any of:

1-(3-(2-(1,2,3,4-Tetrahydro-9H-pyrido(3,4-b)indolyl)methyl)benzoyl)pipridine; or 1-(3-(2-(1,2,3,4-Tetrahydro-9H-pyrido(3,4-b)indolyl)methyl)benzoyl)indoline;

1-(3-(1-(1,2,3,4,4a,5-Hexahydropyrazino(1,2-c)-1,4-benzoxazinyl)methyl)benzoyl)piperidine; or 1-(3-(3-(1,2,3,4,4a,5-Hexahydropyrazino(1,2-c)-1,4-benzoxazinyl)methyl)benzoyl)indoline.

8. A pharmaceutical composition comprising the compound of claim 1, in combination with suitable pharmaceutical carrier, said compound being present in therapeutically effective amount for treating a diseases of the central nervous system.

9. A method of treating a disease of the central nervous system responsive to 5-HT$_1$A receptor antagonism comprising administering to an animal afflicted with such a disease the compound of claim 1 in an amount sufficient to treat such disease.

10. The method of claim 9, wherein the disease is anxiety.

* * * * *